(12) United States Patent
Khatri et al.

(10) Patent No.: US 8,138,236 B2
(45) Date of Patent: Mar. 20, 2012

(54) SOLVENT-FREE MOISTURE ACTIVATED LATENT CURING SURGICAL ADHESIVE OR SEALANT

(75) Inventors: Chetan Anirudh Khatri, Belle Mead, NJ (US); Joseph Zavatsky, Flemington, NJ (US)

(73) Assignee: Ethicon, Inc., Somerville, NJ (US)

( * ) Notice: Subject to any disclaimer, the term of this patent is extended or adjusted under 35 U.S.C. 154(b) by 267 days.

(21) Appl. No.: 12/608,361

(22) Filed: Oct. 29, 2009

(65) Prior Publication Data

US 2011/0105641 A1    May 5, 2011

(51) Int. Cl.
*A61L 24/04*    (2006.01)
*A61K 6/087*    (2006.01)
*C08G 73/04*    (2006.01)

(52) U.S. Cl. .................... 523/118; 528/353; 528/367
(58) Field of Classification Search .................. 523/118; 528/353, 367; 524/32, 37
See application file for complete search history.

(56) References Cited

U.S. PATENT DOCUMENTS

| | | | |
|---|---|---|---|
| 3,267,078 A | 8/1966 | Damusis | |
| 3,793,417 A | 2/1974 | Erikson et al. | |
| 4,430,489 A | 2/1984 | MacMillan et al. | |
| 4,570,270 A | 2/1986 | Oechsle, III | |
| 4,804,691 A | 2/1989 | English et al. | |
| 4,829,099 A | 5/1989 | Fuller et al. | |
| 5,198,524 A | 3/1993 | Bush et al. | |
| 5,874,500 A | 2/1999 | Rhee et al. | |
| 5,990,194 A | 11/1999 | Dunn et al. | |
| 6,166,130 A | 12/2000 | Rhee et al. | |
| 6,328,229 B1 | 12/2001 | Duronio et al. | |
| 6,352,710 B2 | 3/2002 | Sawhney et al. | |
| 6,525,159 B1 | 2/2003 | Okuhira et al. | |
| 6,534,591 B2 | 3/2003 | Rhee et al. | |
| 6,864,350 B2 | 3/2005 | Harris | |
| 6,899,889 B1 | 5/2005 | Hnokewyj et al. | |
| 7,129,300 B2 | 10/2006 | Roby | |
| 7,241,846 B2 | 7/2007 | Roby | |
| 7,259,190 B2 * | 8/2007 | Lykke | 521/146 |
| 7,947,758 B2 * | 5/2011 | Khatri et al. | 523/111 |
| 2002/0165337 A1 | 11/2002 | Wallace et al. | |
| 2003/0012734 A1 | 1/2003 | Pathak et al. | |
| 2004/0023842 A1 | 2/2004 | Pathak et al. | |
| 2004/0219214 A1 | 11/2004 | Gravett et al. | |
| 2005/0053576 A1 | 3/2005 | Tanaka et al. | |
| 2007/0031498 A1 | 2/2007 | Zong et al. | |
| 2008/0039547 A1 | 2/2008 | Khatri et al. | |
| 2008/0039548 A1 | 2/2008 | Zavatsky et al. | |

FOREIGN PATENT DOCUMENTS

| | | |
|---|---|---|
| EP | 1165716 | 10/2004 |
| JP | 2000-104037 | 4/2000 |
| WO | WO 89/00589 | 1/1989 |
| WO | WO 94/03155 | 2/1994 |
| WO | WO 2006/076291 | 7/2006 |

OTHER PUBLICATIONS

Polymeric Biomaterials, 2nd Ed., Marcel Dekker Inc. (2002) pp. 716.
Search Report re: PCT/US2007/075418 dated Jan. 16, 2008.
Search Report re: PCT/US2007/075417 dated Jan. 16, 2008.
International Search Report re: PCT/US2010/053938 dated May 20, 2011.

* cited by examiner

*Primary Examiner* — Tae H Yoon
(74) *Attorney, Agent, or Firm* — David R. Crichton

(57) ABSTRACT

The invention relates to a novel moisture activated solvent-free latent curing adhesive or sealant mixture comprising (1) a selected poly(alkylene oxide)imine, and (2) a selected amine reactive moiety.

11 Claims, 3 Drawing Sheets

Synthesis of Ketimine Ia

Synthesis of Isocyanate Macromer IIa

Curing reactions of the formulation derived from linear ketimine (Ia) and tetraisocyanate of pentaerythritol ethoxylate glutarate (IIa)

SOLVENT-FREE MOISTURE ACTIVATED LATENT CURING SURGICAL ADHESIVE OR SEALANT

FIELD OF THE INVENTION

The invention relates to a novel solvent-free moisture activated latent curing surgical adhesive or sealant mixture comprising two reactive components (1) a ketimine and (2) an amine reactive moiety, both liquid in their neat form; and a novel moisture cured surgical adhesive or sealant comprising the reaction product of the amine, generated from (1), and the amine reactive moiety (2).

BACKGROUND OF THE INVENTION

When surgery is performed and wound closure is completed, there is an unmet need for an adhesive or sealant material that will seal the wound site and prevent fluid leakage in, for example a vessel anastomosis or lung resection. Generally, the key requirements of a tissue adhesive/sealant are:
  (1) The surgical adhesive/sealant must have sufficient adhesive or cohesive strength to bond or seal the tissue repair site.
  (2) Any exothermic process involved in the curing of the adhesive/sealant should not damage the surrounding tissue;
  (3) The adhesive/sealant must not elicit any toxic response by the surrounding healthy tissue and should facilitate the re-growth of new tissue where possible;
  (4) The adhesive/sealant should not liberate harmful degradation products;
  (5) The adhesive/sealant should degrade, and as it does so, it should be replaced by new tissue with minimal scarring; and
  (6) Any biodegradation products should not accumulate in the body but should be eliminated naturally either by excretion or Latent curing adhesive formulations comprising ketimines, electrophilic moieties and solvent are known in the field of surgical adhesives and sealants. For example, a latent curing adhesive may be the mixture of at least two components: one component bearing an electrophilic moiety, such as an isocyanate and nucleophile generating moiety, such as a ketimine. More specifically, the latent curing agent may be present in the two component mixture in a non-reactive form, i.e., latent form, during manufacture, storage and non-use, but may then be converted to a reactive curing agent upon application and use. As an example, the latent curing agent may be converted to a reactive curing agent in the presence of moisture that is present in the environment (e.g. wet tissue in the wound site, or supplied to the site upon use). It is well known in the art, for example, that a ketimine moiety may be used as a latent curing agent that can be converted to a reactive curing agent, i.e., an amine moiety, in the presence of water. After the ketimine moiety has been converted to its amine counterpart, the amine moiety may then react with the second component of the mixture, i.e., a reactive moiety such as an isocyanate, to form the desired cured adhesive and/or sealant. Examples of various ketimine based latent curing surgical adhesives that rely on solvent to be in liquid form under ambient conditions are described in published U.S. patent applications US2008/0039547 A1 and US2008/0039548 A1.

However, the latent curing adhesives described in the prior art are intended for use with the aid of a solvent, and are less ideal for human use as an internal surgical adhesive or sealant.

SUMMARY OF THE INVENTION

The present invention is directed to liquid moisture activated solvent-free latent curing adhesive or sealant mixture comprising a selected poly(alkylene oxide)imine and an amine reactive moiety wherein the poly(alkylene oxide)imine and amine reactive moiety components are liquid under ambient conditions and are present in the adhesive or sealant mixture in their neat forms. Ambient conditions means at approximately human body temperature. The moisture activated solvent-free latent curing adhesive or sealant mixture can further include an effective amount of one or more functional fillers that improve biocompatibility or physicomechanical properties of the mixture.

DETAILED DESCRIPTION OF THE INVENTION

Figure 1:
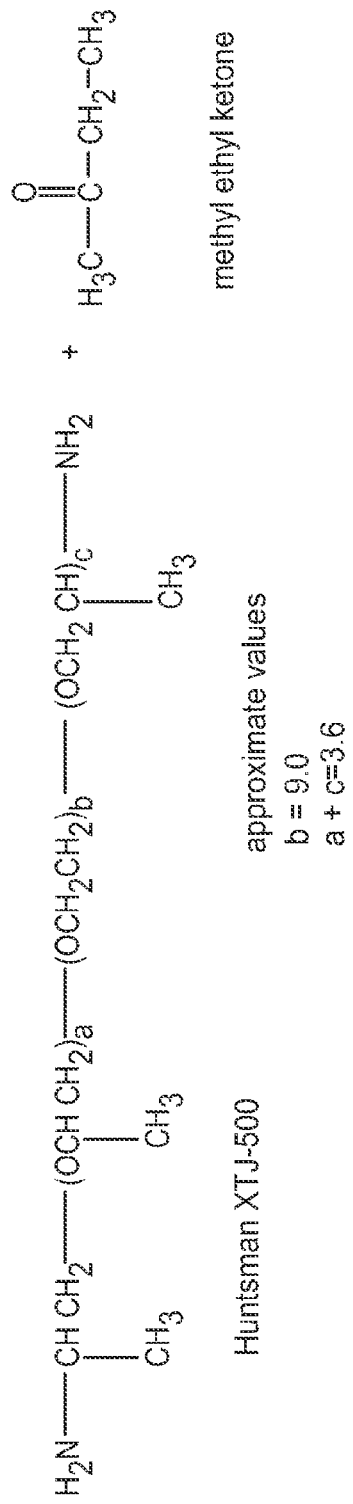
FIG. 1 illustrates synthesis of a liquid ketimine Ia.
Figure 1:
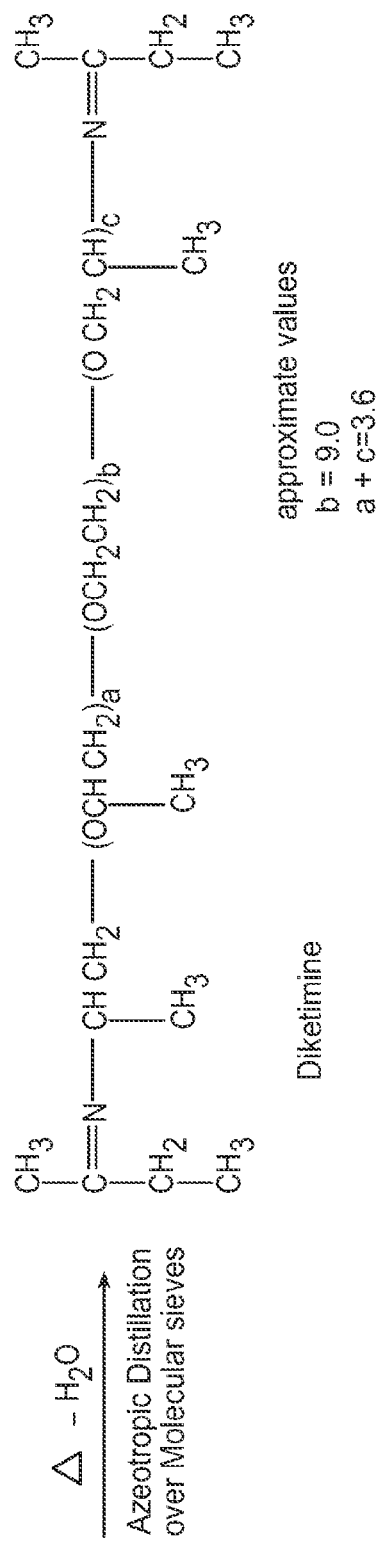
Figure 2:
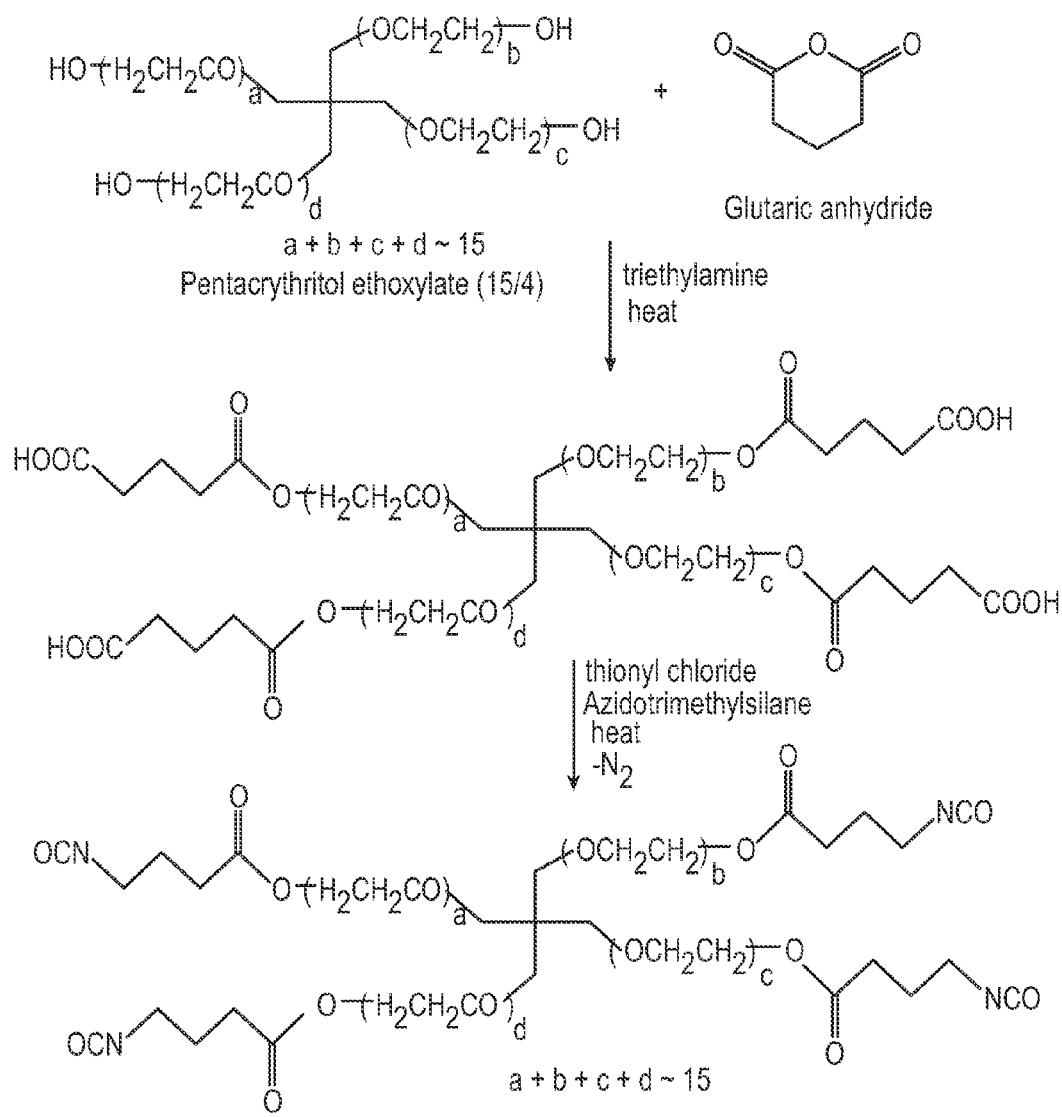
FIG. 2 illustrates synthesis of a liquid amine reactive moiety having an electrophilic group and absorbable ester linkages IIa.

The present invention relates to a novel solvent-free moisture activated latent curing surgical adhesive or sealant mixture comprising two liquid (at ambient conditions) based components (1) a ketimine, and (2) an amine reactive moiety, both liquid in their neat form; and a novel moisture cured surgical adhesive or sealant comprising the reaction product of the amine, generated from (1), and the amine reactive moiety (2). The latent curing ability of the adhesive or sealant mixture, free from solvent, described herein is imparted by blocking a reactive primary amine with a ketone to form a poly(alkylene oxide)imine. The reaction of the poly(alkylene oxide)imine with the electrophilic groups of an amine reactive moiety is relatively slow, such that these two components may be in intimate contact in a mixture, in the absence of moisture, for extended periods of time, i.e., for up to about 5 hours without premature gelling. By comparison, when the two-component mixture is subjected to moisture, the poly (alkylene oxide)imine is "de-blocked" with water to reform the poly(alkylene oxide)amine from which the poly(alkylene oxide)imine is derived within about 30 seconds to 3 minutes, which then immediately reacts with the electrophilic groups of the amine reactive moiety.

The latent curing surgical adhesive or sealant mixture according to the present invention that is liquid and solvent free has multiple medical applications and may be used in many types of surgery, including, but not limited to, cardio-vascular, peripheral-vascular, cardio-thoracic, gynecological, neuro- and general abdominal surgery. The term "solvent-free" as used herein refers to a system, which is completely free of a liquid that solubilizes the prepolymeric components of the surgical sealant mixture, meaning the absence of any organic or aqueous solvents besides the neat surgical sealant mixture.

The latent curing surgical adhesive or sealant described here may be used as an internal surgical adhesive in orthopedic procedures such as anterior cruciate ligament repair, meniscal tear repair (or as a hydro gel for the replacement of the meniscus), posterior capsule reconstruction, rotator cuff repair, and as a bone adhesive. It could also be used as an adhesive for lung volume reduction, patch fixation, subcutaneous tissue repair, and aortic dissection. In particular, it can be used as stomach adhesive for stomach volume reduction, and as adhesive for mesh fixation for hernia repair, drain fixation, valve attachment, attachment for adhesion prevention films, attachment of tissue to tissue (e.g. synthetic or biologic tissue scaffold to tissue, bioengineered tissue to tissue), tissue to device (e.g. mesh, clip, film) and device to device.

Second, the latent curing surgical adhesive or sealant mixture can be used for subcutaneous tissue repair and for seroma prevention in procedures such as mastectomy, breast reconstruction & augmentation, reconstructive or cosmetic abdominoplasty and liposuction, face lift, C-section, hysterectomy in obese patients, orthopedic on thigh region, incisional hernia repair, lipoma excision, traumatic lesions, fistula treatment, graft fixation, and nerve repair.

Third, the latent curing surgical adhesive or sealant can be used as a sealant to attach and seal dural patch products, bile duct, bile leaks in liver bed, bladder leaks, bone graft, burn graft dressing and liquid occlusive dressing. As a sealant, it can be coated on tissue, device, and tissue-device interface and it can be used as dural—cranial sealant, dural—spine sealant, cardio/peripheral vascular sealant, GI sealant (e.g. esophagus, intestine, large organ, pancreas, stomach, and gastric ulcer), lung sealant, soft organ sealant (e.g. liver, spleen, pancreas), bonewax substitute, tumor sealant, staple/glue combination, sealant/hemostats combination, urethra sealant. It can be used in procedures including, but not limited to, gastric bypass, parenchymatous organs resection, tracheostomy, ulcerative colitis diverticulosis, radical prostatectomy, sinus reconstruction, sternotomy, choledochoduodenostomy, and gallbladder (liver) bed sealing, and cholecystectomy.

Fourth, the latent curing surgical adhesive or sealant can be used as a filler or a periurethral bulking agent in procedures including, but not limited to, dead space removal in reconstructive and cosmetic surgeries, (e.g. plastic/cosmetic/reconstructive, face/facial defect, or void filling), urinary incontinence and other gynecologic procedures, anal fissure/fistula, catheter injection into myocardium for treating congestive heart failure, nuclear augmentation, pancreatic/hepatic cyst/fistula obliteration, and pediatric esophageal fistula.

Fifth, the latent curing surgical adhesive or sealant can be used as a matrix for tissue engineering (e.g. tissue scaffolds, delivery matrix for cells, delivery matrix for brachytherapy (radiation therapy) agents, delivery matrix for growth factors, injection matrix for in situ-forming empty cell scaffold, injection matrix for scaffold for delivery of stem cells, cell lysate, or other biologics, bioactives, pharmaceuticals, and nutraceuticals, localization matrix for chemotherapy, and localization matrix for contrast agent.

Sixth, the latent curing surgical adhesive or sealant can be used as an adhesion prevention barrier in procedures such as cardiac, open chest, general surgery, obstetrics and gynecological surgeries, orthopedic surgeries, and spine (e.g. artificial disk).

Seventh, the latent curing surgical adhesive or sealant can be used as an occluding material for embolization (e.g. GI Fistula, cerebral/vascular occlusive brain aneurysm, tubal occlusion, and varicose vein occlusion).

The Ketimine

The liquid ketimine can be an imine macromer, such as a poly(alkylene oxide) imine represented by formula I:

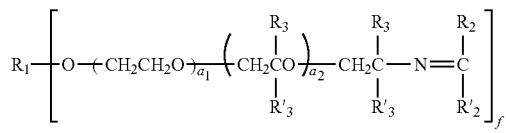

Formula I wherein
$R_1$ is a linear or branched $C_1$ to $C_{14}$ residue optionally having one or more heteroatoms of a polyol that is selected from the group consisting of pentaerythritol, glycerol, tetra(2-hydroxypropyl) ethylenediamine and poly(alkylene oxide);
$R_2$ and $R'_2$ are, independently of one another, a $C_1$-$C_4$ alkyl group, preferably methyl, ethyl, isopropyl or isobutyl groups;
$R_3$ and $R_{3'}$ are, independently of one another, hydrogen, a linear or branched $C_1$-$C_5$ alkyl group, and
for a poly(alkylene oxide)imine sample, the average value for $a_1$ is between 3 and 20, inclusive, preferably between 5 and 10, inclusive; and the average value for $a_2$ is between 0 and 5, inclusive, preferably between 1 and 3, inclusive and the average value for f is between 2 and 6, inclusive, preferably between 2 and 4, inclusive.

The average values for $a_1$ and $a_2$ of poly(alkylene oxide) samples can be determined in conventional manner using NMR or mass spectrometry.

In one embodiment, $R_1$ is an ethylene group and the average value for f of a poly (alkylene oxide)imine sample is 2.

In another embodiment, $R_2$ and $R'_2$ are methyl or ethyl groups, and more preferably, $R_2$ and $R'_2$ are different.

In another embodiment, $R_3$ and $R'_3$ are methyl and hydrogen groups, and more preferably, $R_3$ and $R'_3$ are different.

Alternatively, the liquid ketimine used in the present invention can be synthesized from primary amine containing compounds that include, without limitation, poly (alkylene oxide) amines, lysine, dilysine, trilysine and low molecular weight polyethylene imines that, upon derivatization, yield liquid ketimines. A general synthesis of ketimine from a primary amine is described below.

The synthesis of ketimine functional compounds used for surgical adhesives and sealants is carried out by heating a selected primary amine functional compound in the presence of an excess amount of a selected ketone. To drive the reaction of amine with ketone to completion, water is removed as the reaction proceeds. Water can be removed by adding molecular sieves to the reaction mixture or by adding a solvent that forms an azeotrope with the water then collecting the water in a dean stark trap. In the present invention, the molecular sieves and azeotropic methods are combined through the use of a soxhlet extractor. When conversion of amine to ketimine is complete, the excess solvent is removed by distillation.

An example of a preferred liquid poly(ethylene oxide) imine can be derived from bis(2-aminopropyl) ether of polyethylene glycol as shown below in Ia:

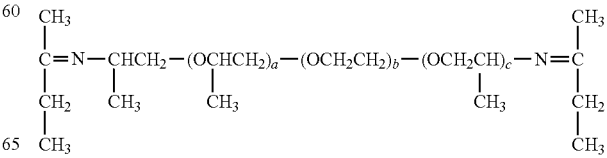

Formula Ia wherein for a poly(alkylene oxide)imine sample, the average value for b is about 9 and the sum of a and c is about 3.6.

The Amine Reactive Moiety

The imine macromers, such as the poly(alkylene oxide) imine represented above by formula I can be used as the latent curing agent for an amine reactive moiety having hydrolytically degradable ester linkages and electrophilic groups that include isocyanate and are represented by Formula II:

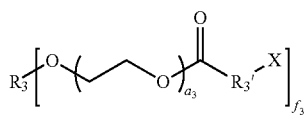

Formula II wherein $R_3$ is a linear or branched $C_1$ to $C_{14}$ residue of a polyol, each $R_3$ is bound to number of $f_3$ reactive pendant chains and wherein the polyol is selected from the group consisting of pentaerythritol, glycerol, poly(alkylene oxide); and $R_3'$ is a linear or branched $C_1$-$C_4$ alkylene group optionally having one or more oxygen atoms; and X is an isocyanate group (i.e. X=NCO).

The number of $f_3$ reactive pendant chains is at least 2 but not greater than 6, preferably at least 2 but not greater than 4; and more preferably is 4.

For each reactive pendant chain, $a_3$ is at least 3 but not greater than 20, preferably at least 3 but not greater than 10. The average value for $a_3$ of liquid reactive amine samples can be determined in conventional manner using NMR or mass spectrometry.

$R_3'$ preferably is —$CH_2CH_2$—, —$CH_2CH_2CH_2$— or —$CH_2OCH_2$—.

In one alternative embodiment, $R_3$ is a residue of pentaerythritol, and the number of $f_3$ reactive pendant chains is 4.

A general method for synthesizing an exemplary amine reactive moiety with degradable ester linkage is described below. An isocyanate with degradable ester linkages can be made by initially reacting a starting alcohol (e.g. pentaerythritol ethoxylate) with a slight excess of anhydride (e.g. glutaric anhydride) with a small amount of catalyst (e.g. triethylamine). After all of the hydroxyl groups are reacted, excess of anhydride is removed. The carboxyl functionality groups are then converted into acid chloride followed by reaction of the acid chloride derivative with a source of azide moiety (e.g.) azidotrimethylsilane and heating to obtain isocyanate with hydrolytically degradable ester linkage. Other hydroxyl terminated polymers that can be used to carry out reactions to form isocyanate terminated prepolymers, include without limitation, low molecular weight linear or branched multi-arm polyols.

To render the amine reactive moiety water-soluble, the molecular weight of amine reactive moiety may range from about 500 to 4,000, preferably from about 1000 to 2000, and more preferably from about 1000 to 1500 and most preferably about 1350.

In a preferred but non-limiting embodiment, X is an isocyanate group, as shown in the isocyanate terminated PEG prepolymer, represented by formula IIa:

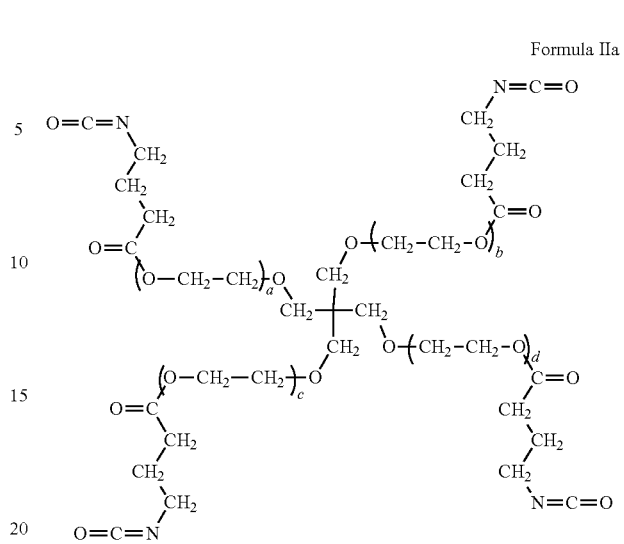

Formula IIa wherein for a liquid poly(alkylene oxide)imine sample, the sum of a, b, c and d is less than 20, preferably about 15.

The Solvent-Free Moisture Activated Latent Curing Surgical Adhesive or Sealant

Figure 3:
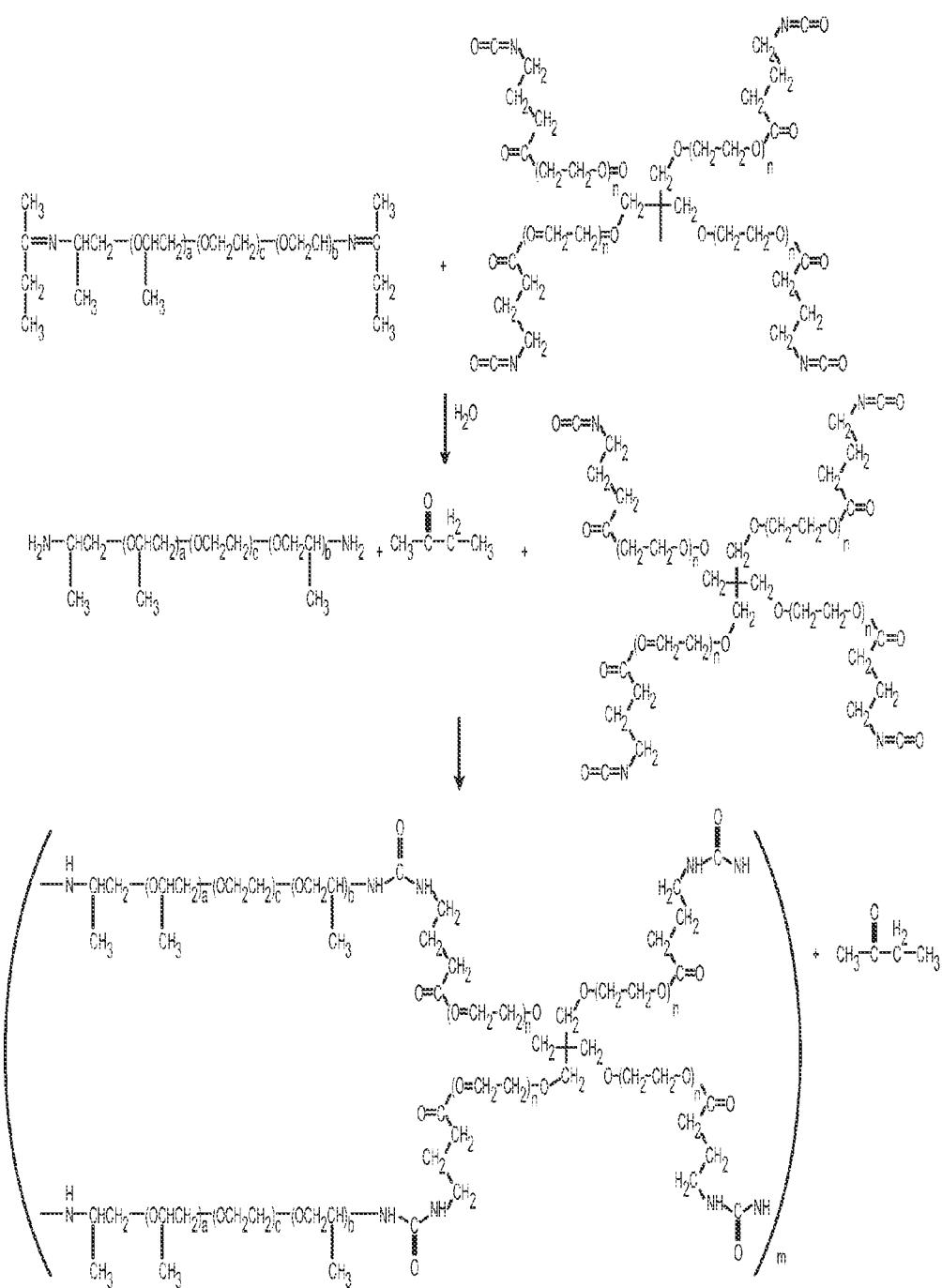
FIG. 3 illustrates the solvent-free moisture activated curing of a hydrolytically degradable liquid isocyanate macromer with a liquid ketimine.

The amine reactive moiety having hydrolytically unstable ester linkages and electrophilic groups and the ketimine remain relatively stable when mixed together, and in the absence of moisture. However, upon exposure to moisture, the ketimine liberates a ketone to form a polyamine, and the polyamine and amine reactive moiety having hydrolytically unstable ester linkages and electrophilic groups react as shown in FIG. 3, to cure in approximately 1-2 minutes. The time to cure can be adjusted by choice of a more or less sterically hindering blocking ketone and the use of an acid catalyst, such as oleic acid.

The moisture activated latent curing adhesive formed via the reaction of poly (alkylene oxide)imine of formula Ia and the isocyanate terminated PEG prepolymer of formula IIa has been designed to be biocompatible and biodegradable by utilizing predominantly PEG backbones in both of the reactants Ia and IIa, and by incorporating hydrolytically unstable ester linkages in the compound of formula IIa that will yield water soluble breakdown products, upon application and use in the human body.

This type of moisture activated latent curing solvent free surgical adhesive or sealant mixture offers significant benefits over the state of the art in terms of tissue adhesion, efficacy, biocompatibility, storage stability and ease of use. By judicious selection of the polymer backbones and the location of the imine end-groups and the electrophiles, various other attributes, for example, the rate of absorption and the degree of water-swellability, etc. can be tailored to suit one's needs.

Additionally, the solvent free surgical sealant adhesives in the present invention can be further formulated with functional fillers in an amount effective to improve biocompatibility and physicomechanical properties, such as thixotropy.

Functional fillers as used herein refer to substances that are used to impart certain desirable characteristics to the adhesive or sealant formulation such as improved rheology, biocompatibility, stability and mechanical performance of the surgical adhesive and sealant. Such fillers can contain functional groups capable of reacting with organic functional groups present in the surgical sealant and adhesive base. Examples of functional fillers include, without limitation, carboxymethyl cellulose, polyvinyl alcohol, bioabsorbable polyesters, collagen, and gelatin.

One potential use for functional fillers in surgical adhesive compositions is to modify, preferably increase, the viscosity of a given surgical adhesive composition. The amount of functional fillers formulated in the solvent free surgical sealant adhesives in the present invention are from about 0.1% to about 5% by weight, preferably from about 1% to about 3% by weight.

The viscosity of the surgical adhesive compositions should be in such a range that the composition can be applied with ease, while still maintaining required mechanical strength. If the viscosity of the surgical adhesive composition is not sufficiently low, addition of the functional filler may result in an unsuitable product. The viscosity of the liquid adhesive base is preferably between 50 and 5000 cP, more preferably between 50 and 1000 cP and most preferably between 50 and 500 cP.

Surgical sealants, with solvent (aqueous or non-aqueous) present due to their instant curing cannot be formulated into high viscosity pastes, as pastes of higher viscosity without the liquid latent curing character as described in the present invention will quickly gel before the two components can be sufficiently mixed, resulting in heterogeneous gelation i.e. clumps of gel mixed with solvent. According to the present invention, the two liquid components bearing the latent curing character can be thoroughly mixed prior to contacting the moisture, thus yielding a homogeneous and uniform surgical sealant adhesives. Examples of functional fillers include, without limitation, carboxymethyl cellulose, polyvinyl alcohol, collagen, gelatin, oxidized regenerated cellulose, bioabsorbable polyesters.

While the following examples demonstrate certain embodiments of the invention, they are not to be interpreted as limiting the scope of the invention, but rather as contributing to a complete description of the invention.

Synthesis of Ketimine Ia, Isocyanate Macromer IIa and their Gelation

Example 1

Synthesis of Ketimine Ia 109.02 g of a polyoxyalkylene diamine (Huntsman ED-600), 168 g of methyl ethyl ketone (MEK) and a magnetic stirring bar are added to a 2 neck, 24/40 ground joint, 500 ml round bottom flask. The flask is placed in an oil bath equipped with a heating coil and temperature controller. To the center neck of the round bottom flask, a soxhlet extractor is fitted. A glass wool thimble filled with activated 4 A molecular sieves is placed within the soxhlet extractor and a reflux condenser is placed on top of the soxhlet extractor with dry $N_2$ flowing in through the condenser. The oil bath is heated to 110° C., at which point, distillation of MEK and its water azeotrope begins. Distillation continued, repeatedly filling the glass wool thimble containing molecular sieves and returning the dried MEK back to the reaction flask. This continuous extraction is allowed to continue overnight. The soxhlet extractor is replaced with a distillation head and the excess MEK is removed, yielding 134.2 grams of a clear, slightly yellow, low viscosity liquid ketimine. Conversion of amine to ketimine is confirmed by NMR.

Example 2

Synthesis of Isocyanate Macromer IIa

In a dry 1 L round bottomed flask are added dry 400 g of pentaerythritol ethoxylate, 270 g of glutaric anhydride and 0.6 g of triethylamine. The reaction mixture is heated to 60° C. under nitrogen and progress followed by NMR until all hydroxyl groups reacted. Excess of anhydride is removed. 245.0 g of purified multi-arm acid intermediate is transferred into a 1 L flask and 200 mL of anhydrous dichloromethane is cannulated into the flask while stirring. To the homogeneous mixture is added drop wise 95.77 g of thionyl chloride via dry syringe and reaction mixture is refluxed for 2 hour. Hydrochloric acid gas generated was neutralized via base trap while continuously flushing reaction mixture with inert gas. An FTIR recorded at this stage showed absence of carboxyl groups. Solvent and excess of thionyl chloride are evaporated under high vacuum and 150 mL of dry toluene is added to the reaction flask followed by slow and careful addition of 117.0 mL of azidotrimethylsilane in small aliquots to the reaction mixture at 75° C. over a period of 3 h. Extreme care must be taken during addition of azidotrimethylsilane. In addition, the nitrogen formed during the reaction must be released continuously. After completion of reaction the mixture is cooled to room temperature, solvent and volatiles are first evaporated under high vacuum at room temperature and then subsequently under high vacuum at 70° C. to obtain 243 g light brown colored liquid. FTIR, proton NMR and isocyanate titration number are in agreement with the final product IIa.

Example 3

Formulation of Linear Ketimine and Tetrafunctional Isocyanate Macromer

A mixture comprising ketimine Ia and the tetrafunctional isocyanate macromer IIa is allowed to react via the scheme shown in FIG. 3. From a glass vial, hermetically sealed with an aluminum rimmed silicone rubber septa, containing methyl ethyl ketimine of polyoxyalkylene diamine was drawn 1 mL of ketimine using an 18 gauge needle, into a 3 ml polypropylene syringe equipped with a leer lock. Excess air was removed from the syringe and the contents were added to another similarly sealed glass vial that contained 1 ml of the tetrafunctional isocyanate macromer. The two components were mixed thoroughly by repeatedly expressing and withdrawing them into and from the second glass vial for ca. 30 seconds, resulting in a clear slightly yellow solution. This solution remained stable liquid for ~2 hours. When expressed onto wet porcine tissue, the solution gelled within one minute to form a solid, clear and strongly adhering hydrogel.

An Ex-Vivo Arterial Anastomoses Model

In this model, anastomoses are performed on porcine carotid arteries conditioned at 37° C. This is followed by pressurizing the sutured artery with saline to slowly increase the fluid pressure inside the sutured artery, until failure is noted by the leaking of fluid from the suture line. The pressure at failure was noted as the baseline and typically ranged between 40-60 mm Hg.

The ketimine Ia, and the tetrafunctional isocyanate macromer IIa are mixed to form a viscous stable liquid, which are then applied to the suture line and allowed to cure. The fluid pressure is increased again and the pressure at failure is noted. The ketimine based sealant cured after being applied to the wet vessels in 2-3 minutes and pressures at failure ranged from 170 to 230 mm Hg in multiple runs.

Example 4

Formulation of Linear Ketimine and Tetrafunctional Isocyanate Macromer and Functional Fillers A 3% gel of carboxymethylcellulose (Hercules 7 MPH) in water is prepared via a combination of mechanical and manual stirring. The resulting gel is lyophilized and the resulting foam is then ground using a Wiley mill and a 60 mesh. The resulting powder is dried in a flat bottomed heavy walled flask with a 40/50 ground joint, overnight under high vacuum.

~0.16 g of the lyophilized, ground and dried carboxymethylcellulose powder is weighed into a 5 ml polypropylene syringe with leur lock. 2 ml of mixed adhesive formulation as described in example 3 in a 3 ml syringe is mixed with the CMC powder by attaching the two syringes via a double sided male leur lock connector and repeatedly expressing and withdrawing the flowable paste from one syringe to the other. When all of the material is moving easily from one syringe to the other, the paste is expressed onto a wet porcine arterial vessel. While the paste in the syringe remains flowable for >1 hour, the paste expressed onto the tissue cures in <1 min to a solid hydrogel.

When used in a bleeding porcine spleen model, the above composition is able to stop mild to moderate bleeding with only 30-60 second tamponade.

What is claimed is:

1. A liquid moisture activated solvent-free latent curing adhesive or sealant mixture comprising a poly(alkylene oxide)imine represented by formula I:

$$R_1 \left[ O \text{---} (CH_2CH_2O)_{a_1} \text{---} \left( \begin{array}{c} R_3 \\ | \\ CH_2CO \\ | \\ R'_3 \end{array} \right)_{a_2} \text{---} \begin{array}{c} R_3 \\ | \\ CH_2C \\ | \\ R'_3 \end{array} \text{---} N \text{=} \begin{array}{c} R_2 \\ | \\ C \\ | \\ R'_2 \end{array} \right]_f$$

Formula I wherein
$R_1$ is a linear or branched $C_1$ to $C_{14}$ residue optionally having one or more heteroatoms of a polyol that is selected from the group consisting of pentaerythritol, glycerol, tetra(2-hydroxypropyl)ethylenediamine and poly(alkylene oxide);
$R_2$ and $R'_2$ are, independently of one another, a $C_1$-$C_4$ alkyl group;
$R_3$ and $R'_3$ are, independently of one another, hydrogen or methyl group and different from one another, and for a liquid poly(alkylene oxide)imine sample, the average value for $a_1$ is between 3 and 20, inclusive; and the average value for $a_2$ is between 1 and 3, inclusive and the average value for f is between 2 and 6, inclusive;

and an amine reactive moiety represented by Formula II:

$$R_3 \left[ O \text{---} ( \quad )\text{---}O)_{a_3} \text{---} \overset{O}{\underset{\|}{C}} \text{---} R_3' \text{---} X \right]_{f_3}$$

Formula II wherein $R_3$ is a linear or branched $C_1$ to $C_{14}$ residue of a polyol, each $R_3$ is bound to number of $f_3$ reactive pendant chains and wherein the polyol is selected from the group consisting of pentaerythritol, glycerol, and poly(alkylene oxide), wherein the number of $f_3$ reactive pendant chains is at least 2 but not greater than 6 and $a_3$ is at least 3 but not greater than 10; and $R_3'$ is a linear or branched $C_1$-$C_4$ alkylene group optionally having one or more oxygen atoms; and X is an isocyanate group, wherein the poly(alkylene oxide)imine and amine reactive moiety components are liquid under ambient conditions and present in the adhesive or sealant mixture in their neat forms.

2. A moisture activated solvent-free latent curing adhesive or sealant mixture according to claim 1 wherein $R_1$ is an ethylene group and the average value for f of a liquid poly(alkylene oxide)imine sample is 2.

3. A moisture activated solvent-free latent curing adhesive or sealant mixture according to claim 1 wherein $R_2$ and $R'_2$ are, independently of one another, methyl or ethyl.

4. A moisture activated solvent-free latent curing adhesive or sealant mixture according to claim 3 wherein $R_2$ and $R'_2$ are different.

5. A moisture activated solvent-free latent curing adhesive or sealant mixture according to claim 1 wherein the number of $f_3$ reactive pendant chains is at least 2 but not greater than 4.

6. A moisture activated solvent-free latent curing adhesive or sealant mixture according to claim 1 wherein the number of $f_3$ reactive pendant chains is 4.

7. A moisture activated solvent-free latent curing adhesive or sealant mixture according to claim 1 wherein $R_3'$ in formula II is —$CH_2CH_2$—, —$CH_2CH_2CH_2$— or —$CH_2OCH_2$—.

8. A moisture activated solvent-free latent curing adhesive or sealant mixture according to claim 1 wherein $R_3$ in formula II is a residue of pentaerythritol, and the number of $f_3$ reactive pendant chains is 4.

9. A moisture activated solvent-free latent curing adhesive or sealant mixture according to claim 1 further comprising an effective amount of one or more functional fillers that improve biocompatibility or physicomechanical properties of the mixture.

10. A moisture activated solvent-free latent curing adhesive or sealant mixture according to claim 9 wherein the one or more functional filler is added in an amount effective to increase the rheology, biocompatibility, stability and mechanical performance of the surgical adhesive and sealant.

11. A moisture activated solvent-free latent curing adhesive or sealant mixture according to claim 9 wherein the one or more functional filler is selected from the group consisting of carboxymethyl cellulose, polyvinyl alcohol, bioabsorbable polyester, collagen and gelatin.

* * * * *